(12) United States Patent
Sukeda et al.

(10) Patent No.: US 7,287,430 B2
(45) Date of Patent: Oct. 30, 2007

(54) METHOD OF EVALUATING CONNECTED PORTIONS, METHOD OF CONNECTING ELECTRICAL WINDING CONDUCTORS AND APPARATUS THEREFOR

(75) Inventors: Masami Sukeda, Takahagi (JP); Yasuaki Kageyama, Hitachi (JP); Norihiro Watanabe, Hitachi (JP); Shinya Odajima, Hitachi (JP); Hideo Tanahashi, Hitachi (JP); Masahiro Koike, Hitachi (JP); Yoshinori Musha, Hitachiota (JP); Kazutoshi Ikeda, Hitachi (JP)

(73) Assignees: Hitachi, Ltd., Tokyo (JP); Hitachi Engineering Co., Ltd., Hitachi-shi (JP)

( * ) Notice: Subject to any disclaimer, the term of this patent is extended or adjusted under 35 U.S.C. 154(b) by 156 days.

(21) Appl. No.: 11/126,239

(22) Filed: May 11, 2005

(65) Prior Publication Data

US 2006/0114002 A1    Jun. 1, 2006

(30) Foreign Application Priority Data

May 12, 2004    (JP) .............................. 2004-142327

(51) Int. Cl.
*G01N 29/04* (2006.01)
(52) U.S. Cl. ............................ 73/588; 73/600; 73/602; 73/620
(58) Field of Classification Search .................. 73/588, 73/620, 622, 633, 640, 644, 634, 621, 602, 73/600
See application file for complete search history.

(56) References Cited

U.S. PATENT DOCUMENTS 3,303,418 A * 2/1967 Rose .......................... 324/718

3,777,552 A    12/1973 Fletcher et al.
3,921,440 A * 11/1975 Toth ............................ 73/622

(Continued)

FOREIGN PATENT DOCUMENTS

JP    9-210971    8/1997

(Continued)

OTHER PUBLICATIONS

XP001207222; "Fehlergrossenbestimmung Bei Der Ultraschallprufung Von Hart-Und Hochtemperaturlotverbindungen", Crostack et al., Schweissen und Schneiden 40, No. 11, Nov. 1988, pp. 564-569.

(Continued)

*Primary Examiner*—Hezron Williams
*Assistant Examiner*—Jacques M. Saint-Surin
(74) *Attorney, Agent, or Firm*—Mattingly, Stanger, Malur & Brundidge, P.C.

(57) ABSTRACT

A method of connecting hollow conductors with a brazing alloy employs a measuring mechanism 10 for measuring a connecting state of a connecting portion after brazing hollow conductors. The measuring mechanism comprises a scanner 101 and a holder 19, which are separated in advance, so that the mechanism can be installed in a narrow space. A display mechanism 20 displays measuring results as tow-dimensional patterns, and the evaluation mechanism 30 evaluate the connecting portions by an area of the defects and an integral length of sound portions. A judgment mechanism 40 evaluates relative relation of the measuring results with causes-and-defects, which are previously stored, and shows the cause of the defect.

27 Claims, 15 Drawing Sheets

U.S. PATENT DOCUMENTS

| | | | | |
|---|---|---|---|---|
| 4,218,922 A | * | 8/1980 | Ensminger | 73/588 |
| 4,446,736 A | * | 5/1984 | Jackson | 73/600 |
| 4,827,487 A | * | 5/1989 | Twerdochlib | 374/152 |
| 4,961,347 A | * | 10/1990 | Arakawa et al. | 73/644 |
| 5,426,980 A | * | 6/1995 | Smith | 73/644 |
| 5,509,320 A | * | 4/1996 | Forster | 73/866.5 |
| 6,912,905 B2 | * | 7/2005 | Abbasi et al. | 73/588 |
| 6,945,113 B2 | * | 9/2005 | Siverling et al. | 73/622 |
| 2005/0005700 A1 | | 1/2005 | Abbasi et al. | |

FOREIGN PATENT DOCUMENTS

| | | |
|---|---|---|
| JP | 09210972 | 8/1997 |
| JP | 2001 343367 | 12/2001 |
| JP | 2001-343367 | 12/2001 |

OTHER PUBLICATIONS

"Non-Destructive Inspection", vol. 39, No. 9, 2-17 by S. Hirose, et al. pp. 799-800.

"Non-Destructive Inspection", vol. 39, No. 9, 2-16 by S. Hirose, et al. pp. 797-798.

* cited by examiner

FIG. 15

| No. | A | B |
|---|---|---|
| PATTERN NAME | STRIPE DEFECT | PENINSULA DEFECT |
| TYPICAL PATTERN |  |  |
| STATUS | LARGE CONTINUOUS DEFECT IN THE CENTER | LARGE DEFECT AT SPECIFIC POSITION |
| CAUSE: IMPROPER BRAZING MATERIAL | | |
| CAUSE: IMPROPER SUPPLY METHOD OF BRAZING ALLOY | △ | △ |
| CAUSE: INADEQUATE TEMPERATURE DISTRIBUTION | △ | ◎ |
| CAUSE: EXCESSIVE HIGH HEATING TEMPERATURE | | |
| CAUSE: INSUFFICIENT HEATING (LOW TEMPERATURE) | ◎ | |
| CAUSE: IMPROPER GAP | ○ | ○ |
| CAUSE: INADEQUATE PRE-TREATMENT | △ | △ |

METHOD OF EVALUATING CONNECTED PORTIONS, METHOD OF CONNECTING ELECTRICAL WINDING CONDUCTORS AND APPARATUS THEREFOR

CLAIM OF PRIORITY

This application claims of priority from a Japanese application Ser. No. 2004-142327, filed on May 12, 2004, the content of which is hereby incorporated by reference into this application.

FIELD OF THE INVENTION

The present invention relates to a method of connecting electrical winding conductors for large capacity electric magnets, generators and motors, and more particularly to a method of improving connecting quality of brazing.

RELATED ART

Electrical winding of large scaled electric apparatuses have been manufactured by assembling a number of shaped turns of winding conductors, in general. For example, internal cooling windings have a structure wherein each of the windings has a continuous hollow through which low temperature pure water flows to cool it. As shown in FIG. 3, a pair of conductors 1 each of which has a continuous hollow 3 is assembled with a connecting sleeve 2 and a brazing alloy wire 7 such as an alloy containing copper, silver, phosphor, etc is fed to fill the gaps between the connecting sleeve 2 and the conductors 1, while heating the connecting sleeve 2 and melting the brazing wire 7 with a propane gas burner 4.

Brazing work greatly depends on experience and skill of workers; internal defects in the brazed portion after brazing are detected by an X-ray transmittance inspection or ultrasonic wave inspection. Since the gap into which the brazing alloys permeate is only about 0.05 mm, the X-ray transmittance inspection is applied to such a thin conductor as 1 mm or less. Therefore, the X-ray inspection was not appropriate for such a thick conductor as having 2 to 10 mm.

A connected interface evaluation method by the ultrasonic wave inspection using an ultrasonic wave C scope is known as disclosed in non-patent publication No. 1. In this method, an aluminum plate and a copper plate are brazed by a method of superimposed brazing. Probing results on both faces are displayed on a C scope. A measured error is 0.1 to 0.3 mm with respect to a size of defects of 0.9 to 4.6 mm at a peeling destruction face.

In an inspection apparatus of connected portions of clips of water cooled stator bars of a turbine generator (Patent publication No. 1), an ultrasonic wave probe is moved in the axial direction of the bars, while the probe is rotating around the connected portion; the detected reflection wave signals and position information are processed by a computer. Since a scanner is set to a screw position of the object to be inspected, an automatic inspection can be realized.

(Patent publication No. 1) Japanese patent laid-open No. 2001-343367

(Non-patent publication No. 1) "Non-destructive Inspection", vol. 39, No. 9, 2-17

Since the brazing alloy permeates into the brazing portion by the action of surface tension of a melted brazing alloy in the electrical machines, a gap between a conductor and sleeve of 0.05 to 0.25 mm is used in general. The diameter is the same as in the case of conductors to be brazed having a thickness of about 1 to 10 mm. The defects such as portions where the brazing alloy does not permeate, bubbles occurred in the brazing alloy, empty nests (subsided ball like nests), cracks in the brazing alloy, etc should be thinner than the thickness of the brazing gap. Since the defects have a large area and a large length, but have a very small thickness, a detection technology for the very thin defects is demanded.

Since the detection limit of the X-ray transmittance inspection method is demanded to be 2% or more of the total thickness of the conductor and the sleeve of 0.05 to 0.25 mm, the detection of a defect of 0.05 mm thick was impossible in the case of a conductor of a thickness smaller than 2.5 mm.

The ultrasonic wave probing of the brazed portion is theoretically possible, as mentioned above. However, in electrical windings of the electromagnets or generators, the brazing portions are formed at narrow portions where the turns of the windings are often located and there are different angles of the connecting portions in order to increase a space factor. Therefore, it has been desired that an ultrasonic probing method or system is applicable to the narrow portions.

There are various types of defects caused by brazing; the evaluation result of the electrical windings should satisfy electrical and mechanical requirements. Particularly, the inspection of defects in the brazed portion should be done from the viewpoints of an area and length of the defects so as to prevent leakage of a cooling liquid flowing through the hollow in the conductor.

Various causes are involved in formation of the defects; skill of workers, equipment used and conditions for the equipment, conditions of conductors and brazing alloys may be involved. In actual jobs, an evaluation method or system is necessary for evaluating by observing the interior state of the brazed portions to pick up characteristics and to find out the causes of the formation of the defects so that the evaluation results can be reflected on instructions to the repairing work and on achievement of skill of the workers.

SUMMARY OF THE INVENTION

An object of the present invention is to provide, in light of the above-mentioned problems, a method of conducting an accurate evaluation of defect portions of the connecting portions, which are electric conductive and the connecting portions can keep quality that withstand sufficiently a mechanical power, and also provide a method and apparatus for connecting electrical winding conductors that displays an appropriate repairing guidance.

In order to achieve the above-mentioned object, a method of connecting electrical winding conductors comprising connecting electrical windings each having a continuous hollow with a brazing alloy is characterized in that a connected portion is probed with ultrasonic wave; the sound portion and defect portion are displayed, and the portions are evaluated in accordance with predetermined criteria.

The electrical winding conductors to be connected are aligned to constitute pairs and each of the pairs is aligned in a longitudinal direction. At least one of the conductors of the pair may have a continuous hollow extending in a longitudinal direction.

According to the present invention, since the quality of the defect having a very thin thickness can be electrically and mechanically evaluated, the conductive state and possibility of water leakage in the connecting portion (brazing portion) can be presumed. So, the accuracy of evaluation of the connecting increases. Further, it is possible to pursue working conditions for acquiring high stable quality of connecting and to confirm the degree of achievement skill of workers.

Since the scanner for moving the probe of the measuring mechanism and the holder for fixing the scanner are separated into at least two, and then they are assembled after the installment, it is possible to conduct measurement in a narrow portion.

Since the measurement mechanism is provided with a bottom echo standard gate, it is possible to conduct an accurate and easy detection even in the case of relatively thin defects.

BRIEF DESCRIPTION OF THE DRAWINGS

FIG. 15 is a pattern table of examples of classified patterns based on causes-and-defects for judging of the connecting portion in Example 1.

EXPLANATION OF REFERENCE NUMERALS

1; conductor having a continuous hollow of electrical winding conductor of a generator, 2; sleeve for connecting conductors, 3; hollow in the conductor, 4; gas burner, 5; groove for placing a brazing alloy, 6, 7; brazing alloy, 8; solidified brazing alloy, 9, 9'; defects formed in the brazing alloy, 10; measurement mechanism, 11; ultrasonic wave probe, 12; rotating ring, 13; rotating supporting plate, 14; driving section, 15; supporting rod, 16; rotating shaft, 17; motor, 18; motor, 19; holder, 20; display mechanism, 21; screw hole, 22; cramping bolt, 23; sound portion, 24, 25, 25'; defects, 26; phase connection of electrical winding of a generator, 27; lead of the electrical winding of the generator, 28; solid conductor, 101; scanner.

DETAILED DESCRIPTION OF THE PREFERRED EMBODIMENTS

In the following, the embodiments of the present invention will be explained by reference to the drawings.

Figure 1:
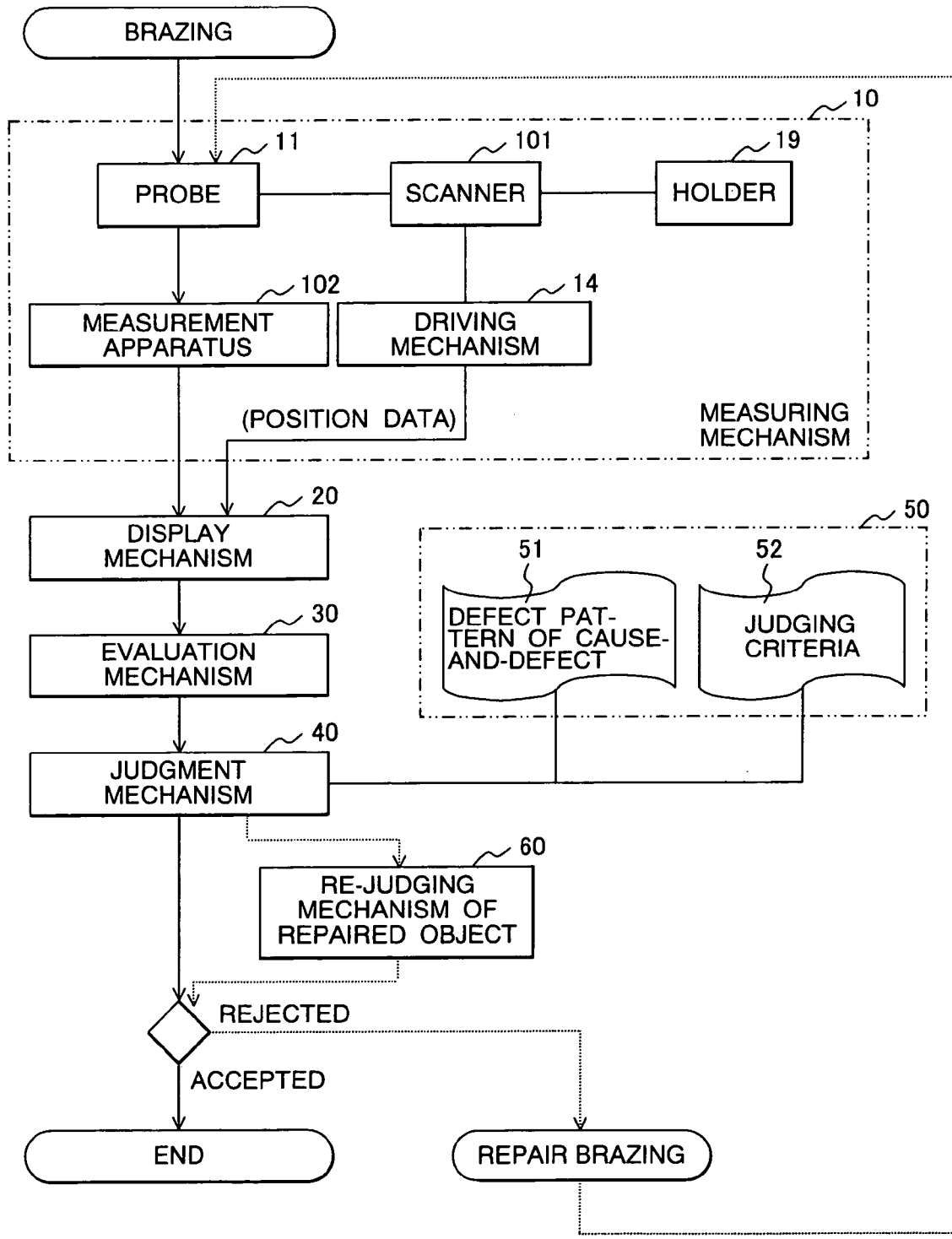
FIG. 1 is a block diagram showing Example 1 of an electrical winding connecting apparatus.

The first embodiment (hereinafter referred to as embodiment 1) according to the present invention is explained. FIG. 1 shows a block diagram of a connecting evaluation apparatus of electrical winding conductors, wherein the blocks are shown in accordance with processing procedures.

The connecting evaluation apparatus comprises an ultrasonic wave probe 11, a scanner 101, a measurement mechanism 10 including measurement device 102, etc, a display section 20 for displaying measurement results in the form of patterns, and an evaluation mechanism 30 for outputting the sound portion or defect portion of the measurement results as a length or an area. Further, the evaluation of the connecting portions are judged based on the predetermined judging standards or criteria; if the judging result can not meet the judging standards, similarity and relationship between the displayed patterns and the cause-and-defect patterns that are stored in advance are investigated, thereby to choose patterns with a high correlation. This investigation is carried out by a judging mechanism 40. The cause-and-defect patterns 51 and judging standards 52, which are capable of reference to the judging mechanism 40 are stored in the memory device 50.

At first, brazing starts; then the connecting portion is inspected by an ultrasonic wave inspection; the results are displayed on a screen in the form of patterns. A length and area of the sound portions and defect portions are measured on the screen. Then, the connecting portions are judged based on predetermined judging standards 52 to determine the connecting portions as "accepted" (sound) or "not accepted" (defect).

If the judging result is "not accepted", repair brazing is carried out. Thus, measurement of the connecting portions is conducted by the measurement mechanism 1. The measurement results are displayed on the screen as patterns. Again, the evaluation and judging are carried out. The difference between the previous connecting and the repaired connecting is detected by the repaired portion judging mechanism 60 to find out whether the repair brazing was effective or a further re-brazing is necessary. The repaired portion judging mechanism 60 pursues conditions of works and equipment and optimization of brazing materials; when the quality is satisfactory, the brazing repairing is finished.

There are various types of defects formed in brazing, such as voids or stripes caused by permeation shortage of a brazing alloy, narrow scratches, etc. The shapes and properties of the defects may change according to shapes of the parts to be connected, workability, equipment used, skills of the workers, etc. Accordingly, if the connecting portions do not satisfy the standards or criteria, it is necessary to predict plural cause-and-defects and to determine optimum conditions in advance. In the present invention, the countermeasures are selected based on database of the actual jobs.

Figure 2:
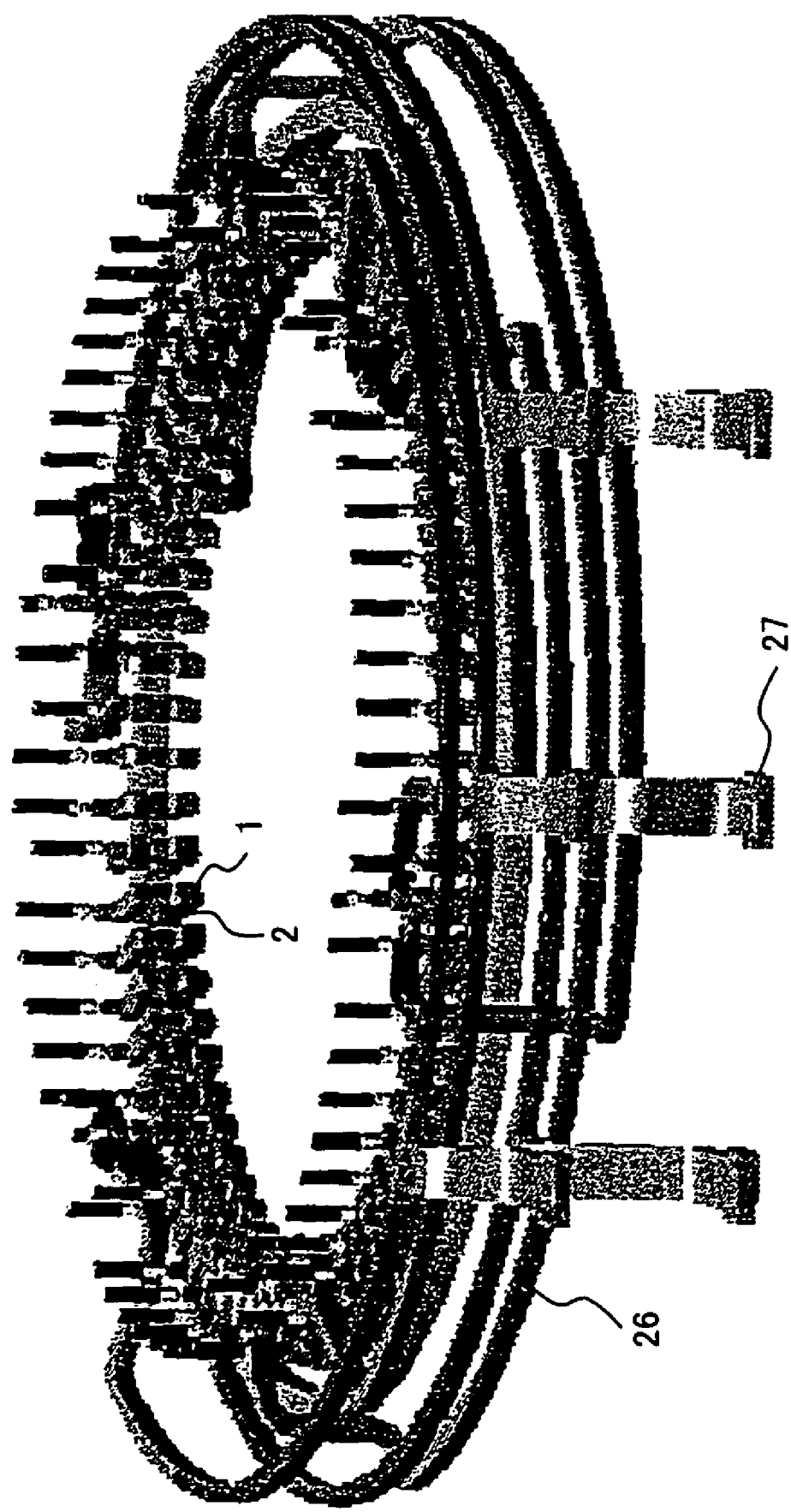
FIG. 2 is a perspective view of a stator winding of a generator to which the present invention is applied.

FIG. 2 shows a perspective view of a stator winding of a turbine generator to which the present invention is applied. This is an example of an end portion where connecting portions adjoin each other. 26 denotes a phase connection winding of the generator winding, and 27 denotes leads of the windings. The end portions of the copper windings having hollow through which pure water flows to cool the windings are connected by means of connecting sleeves made of copper. The plural connecting portions gather at a particular position. The connected conductors constitute electrical windings and output terminals connected to leads 27 by means of phase connecting windings. Pure water for cooling the windings flows through the hollow of the windings, and the cooling water is guided to the adjoining windings.

Figure 3:
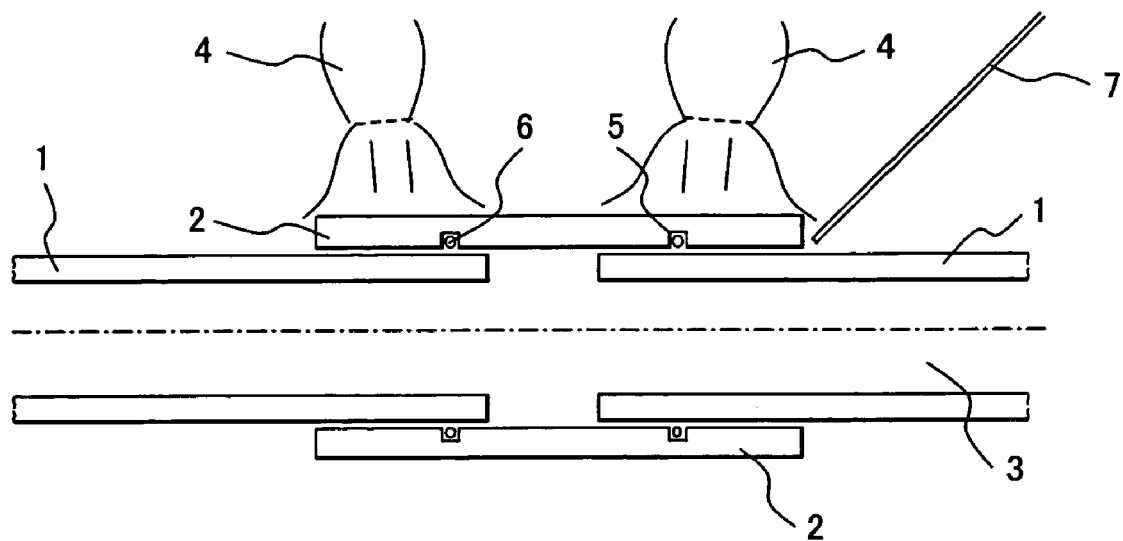
FIG. 3 is a sectional view of a connecting portion of the electrical winding before brazing.

FIG. 3 shows a cross sectional view of a structure of a connecting portion before connecting. A sleeve 2 is provided with grooves 5 in their inner faces that face the hollow conductors 1. The grooves 5 are filled with a brazing alloy 6 made of silver alloy containing copper, etc. The sleeve 2 and the conductors 1 are machined to form a gap between the sleeve 2 and the hollow conductor 1 having a depth of, normally, 0.05 to 0.25 mm. The connecting portions are heated with burners 4 to melt the brazing alloy 6 in the grooves to fill the gaps between the sleeve 2 and the hollow conductors 1 by the action of the wettability and surface tension, thereby to conduct brazing. The heating method is, in addition to the above-mentioned one, an induction heating method, a resistance heating method, etc; any heating methods are within the scope of the present invention.

If there is a shortage of brazing alloy as the melting goes on, the brazing alloy wire 7 is supplied from the end portion of the sleeve as shown in FIG. 3. The sleeves may be divided into pieces or sleeves may be omitted by machining the end portions of the hollow conductors to be a step structure; these methods are within the scope of the present invention.

Figure 4:
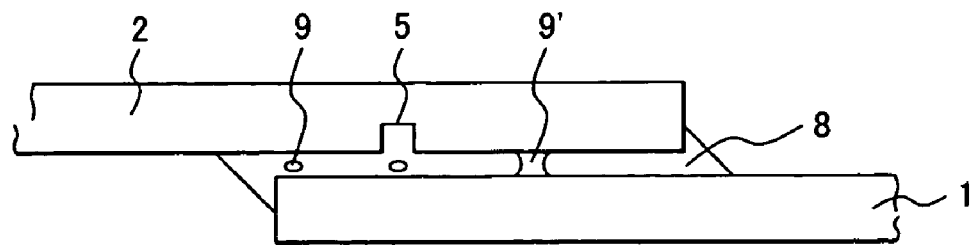
FIG. 4 is a cross sectional view of a connecting portion of the electrical winding after brazing.

FIG. 4 shows a partial enlarged sectional view of the connected portion. In the connected portion, there may be voids 9 in the solidified brazing alloy 8, defects 9', which are caused by poor wettability.

Figure 5:
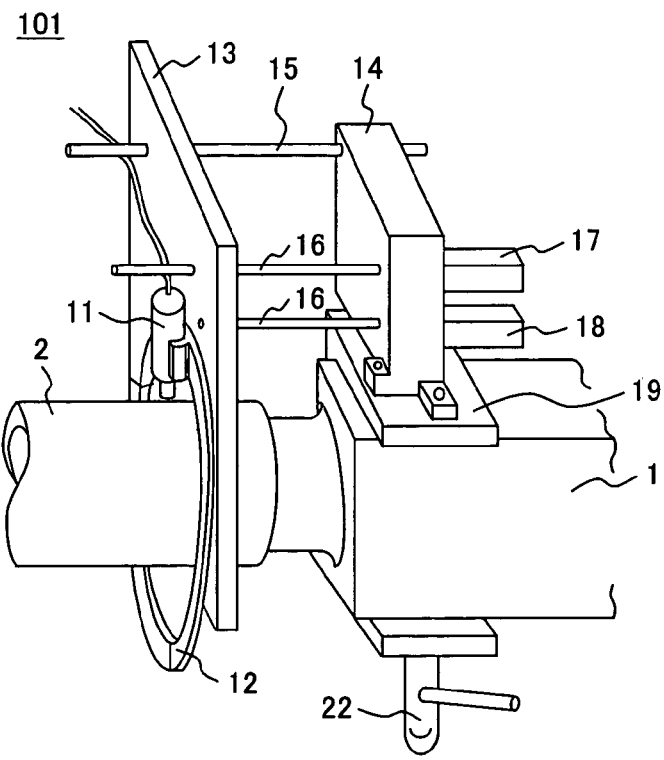
FIG. 5 is a perspective view of an ultrasonic probe apparatus for measuring the connecting portion according to Example 1.

FIG. 5 shows a perspective view of a measurement mechanism, which is provided with a measuring device for measuring the state of brazing. An ultrasonic probe 11 for detecting the connecting state and a divided rotating ring 12 for supporting the probe 11 and a supporting plate 13 for rotatably moving the rotating ring 12 in the circumferential direction are disposed around the brazing position of the sleeve 2.

Further, the measurement mechanism is provided with a driving section 14 including a gear 5, a supporting rod 15 connected to the rotating supporting plate 13 for determining the position of the mechanism, a scanner 101 having a rotating shaft 16 for transmitting driving force to the rotating supporting plate 13 and motors 17, 18, and a dividable holder 19 for supporting the scanner on an appropriate position of the outer periphery of the sleeve 2.

The probe 11 and the driving section 14 are connected by means of a connecting conductor to the measurement mechanism, so that the positioning of the measurement mechanism is performed and measured data is taken into the measurement mechanism 10. The data is processed by the display mechanism 20, evaluation mechanism 30, judging mechanism 40, etc.

Figure 6:
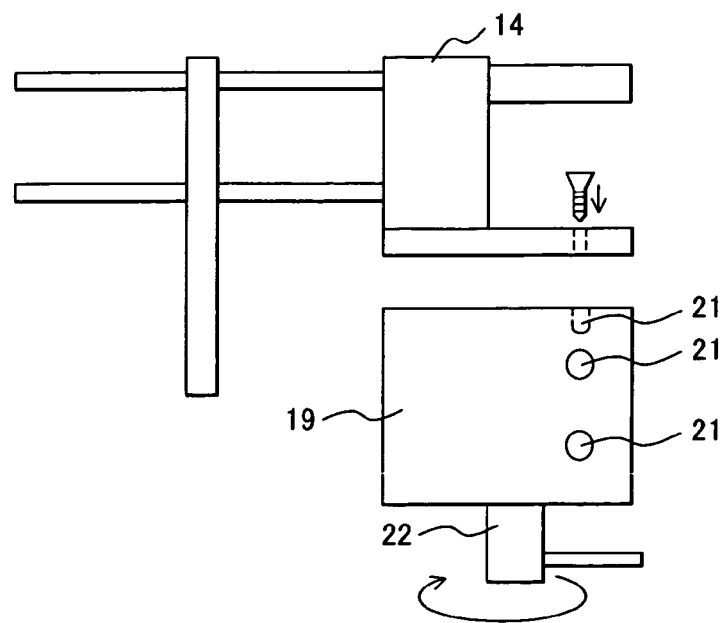
FIG. 6 is a side view of a holder used in measuring the bonging portion of Example 1.
Figure 7:
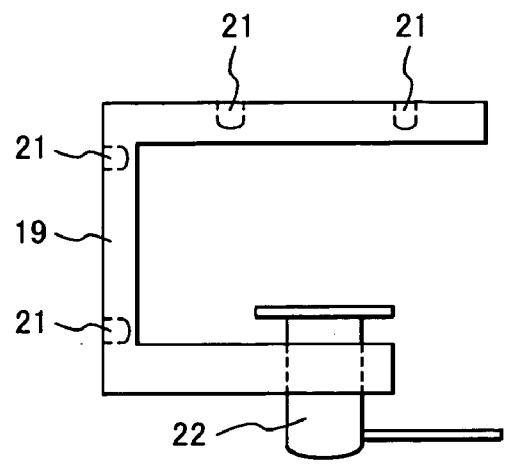
FIG. 7 is a side view of another example of the holder used in measuring the connecting portion.
Figure 8:
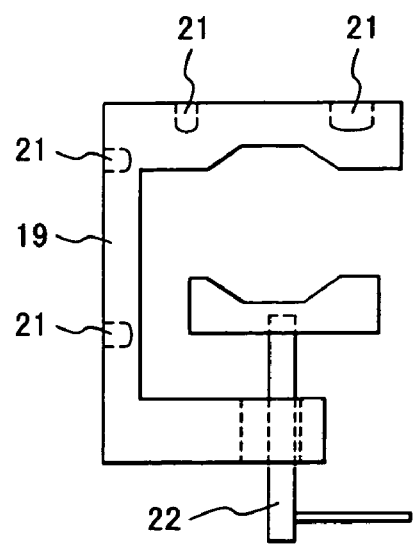
FIG. 8 is a side view of still another example of the holder used in measuring the connecting portion.

FIG. 6 shows a structure of the holder. The holder 19 has screw holes 21 for fixing the scanner. The holder 19 should be firmly fixed to the sleeve 2 in accordance with the shape or angle of the sleeve 2. A proper one is selected from FIG. 7 and FIG. 8.

If the holder 19 and the scanner 101 are united, workers do not put their hand into the narrow portion of the stator winding, and it is difficult to screw the bolts. Further, since an angle between the opening of the rotating supporting plate 13 and the opening of the holder is normally different by 90 degrees, screwing for fastening and assembling are difficult to do.

Thus, the holder 19 and the scanner 101 are separated in advance. The holder 19 is inserted from the side of the sleeve 2 or the conductor 1 and is fastened by a screw 22. The scanner 101 is assembled from the upper direction on the holder 19 and is fastened at a screw hole 21. Numeral 22 denotes a cramp bolt. By this structure, it is possible to conduct an assembling job with minimum obstacles. If the number of the objects of measurement, it is possible to improve efficiency of job, when a number of the holders is prepared in advance.

Figure 9:
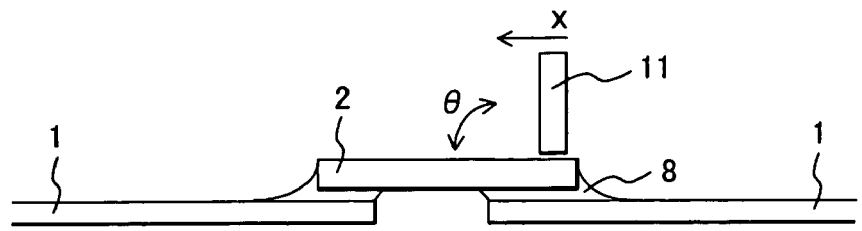
FIG. 9 is a cross sectional view showing a measuring state of the connecting portion.

FIG. 9 shows the state of measurement. The ultrasonic probe 11 is moved in the circumferential direction (θ) and a longitudinal direction (x), and data on designated matrixes are continuously and automatically taken up. The probe 11 has a vibration element, which transforms between electric signals and ultrasonic signals. A vibration element for signal oscillation and a vibration element for signal receiving may be united or separated. An incidental angle of ultrasonic wave signal to the object may be perpendicular or diagonal.

Figure 10:
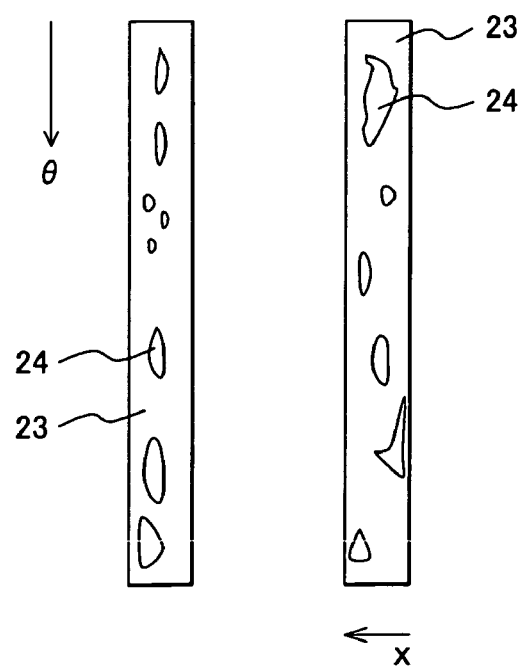
FIG. 10 is a displayed pattern showing the measuring results of the connecting portion in Example 1.

FIG. 10 shows an example of a display pattern of the display mechanism. The displayed pattern is displayed on a two-dimensional plane by developing memorized data, which are obtained by such a manner that the display mechanism 20 plots minute division measurement data on many brazing points of an annular shape.

Figure 11:
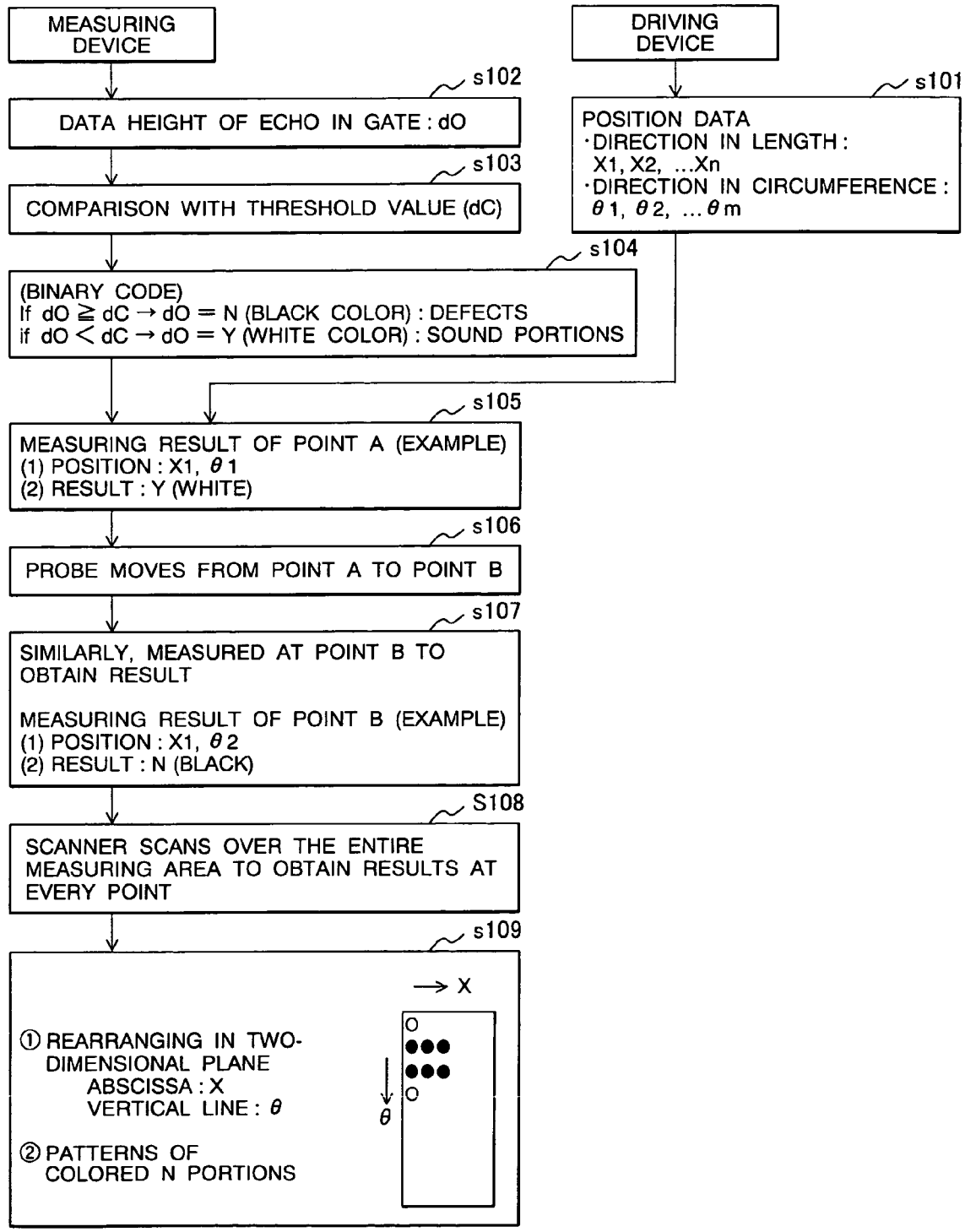
FIG. 11 is a flow chart of an ultrasonic wave probe method for the brazing portion in Example 1.

Then, the operation of the connecting evaluation apparatus for electrical windings according to the present invention will be explained in detail. FIG. 11 shows a flow chart of from measurement to display. The driving mechanism 15 gives position signals ($X_1$, $X_2$, ... $X_n$) in a lengthwise direction and position data ($θ_1$, $θ_2$, ... $θ_n$,) of the object for the probe 11 (s101).

The measurement device 102 that receives reflecting wave signals from the probe 11 to produce data of a depth of the predetermined measuring object as d0 of a peak height (s102). The d0 is compared with dc, which is evaluated as an effective threshold (s103) so as to avoid influence of noise at the time of measurement. If the value is larger than dc, the portion is judged as a defect or "not accepted"; if the value is smaller than dc, the portion is judged as being sound or "accepted" (s104) in a binary digit processing.

A defect "N" is displayed as a black dot and a sound portion "Y" is displayed as a white dot. Take a point A as a measurement position, for example, the position data is $X_1$, $θ_1$; since the height d0 of the echo is in relation of d0<dc, the result is "Y", which is white (s105).

Next, the scanner moves the probe 11 to the point B ($X_1$, $θ_2$), and the measurement at the point B is carried out (s106). As a result, "N", which is black is obtained (s107). This processing is continuously executed within a designated area (s108).

The thus obtained data is displayed on a two-dimensional coordinate (X, θ) (s109). As a result, defect portions (black) and sound portions (white) are developed on a plane. By forming steps to the threshold values dc, it is possible to easily recognize the extent of the height dc of echo with respect to the defect portions.

Figure 12:
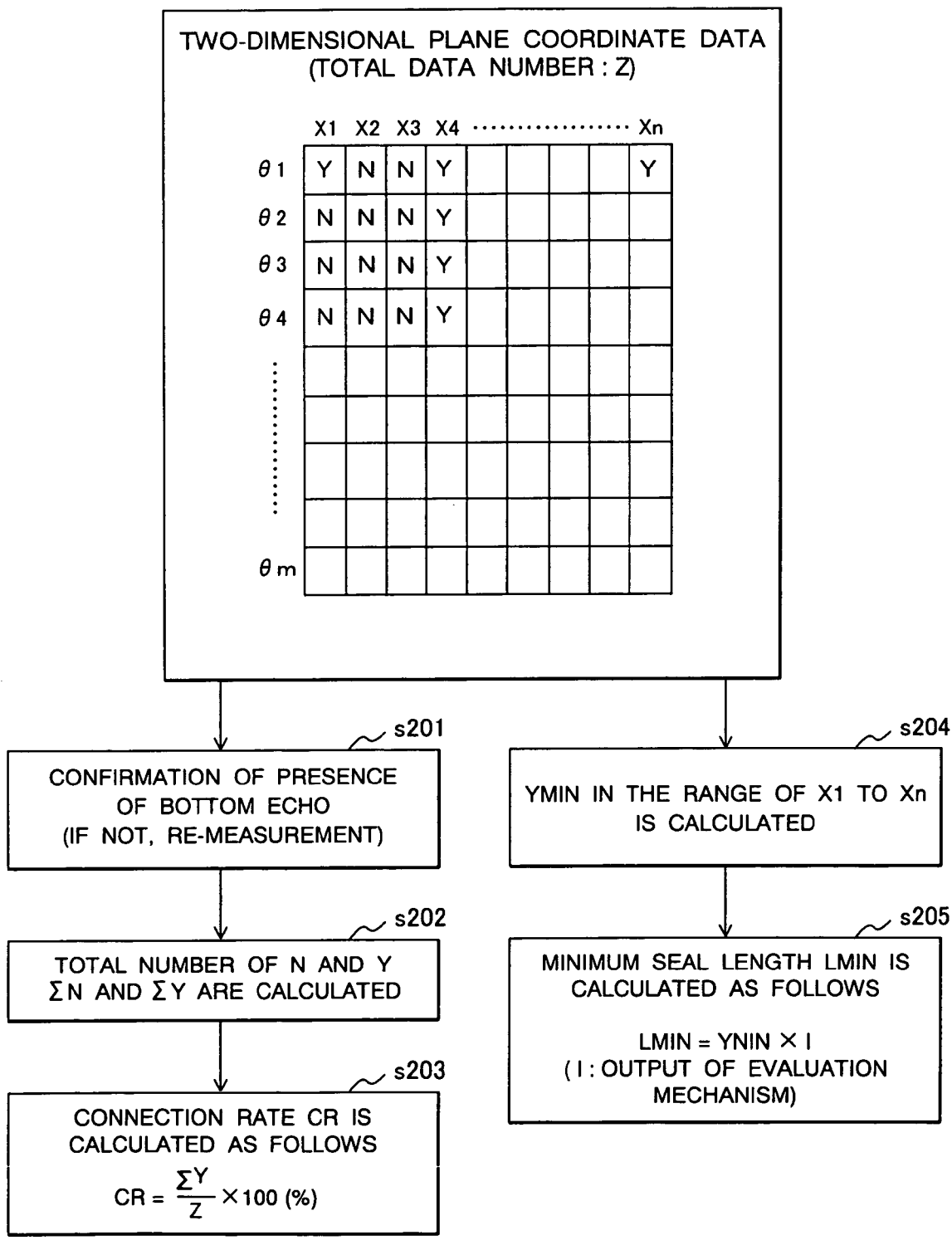
FIG. 12 is a flow chart of an evaluation method for connecting of the electrical winding in Example 1.

FIG. 12 shows an evaluation mechanism. The evaluation mechanism 20 stores Z number (n×m) of data in the two-dimensional plane coordinate. At first, among the data, the data "Y" is investigated whether the evaluation is correct or not. That is, it is confirmed whether ultrasonic wave signals from the probe 11 correctly arrive at brazing portions of the conductors or not. This judgment is done by judging whether reflecting signals (so-called bottom echo) from the surface of the hollows of the conductors are measured in the data of "Y" portions (s201).

If the brazing portions are sound, the ultrasonic wave signals transmit to the sleeve 2 and the hollow conductor 1; they reflect at the surface of the hollow and should be measured as the bottom echo. If the bottom echo is not detected, measurement must be conducted again. This is an inspection of measurement data; if an inspecting person has already done this inspection separately, this step can be omitted in the procedure shown in FIG. 11.

Among the data thus inspected, the total numbers ΣN of N and ΣY of Y are counted, respectively (s202). As a result, connected rate CR at the connecting portion is expressed by ΣY/Z×100(%) (s203). That is, the connected rate CR decreases as the area of defect portion Z increases. Z is shown in FIG. 12, which is used to mean the number of total data represented by Z=ΣN+ΣY=m×n.

The shortest route from X1 through Xn on the two dimensional coordinate wherein the total number ΣY is minimum is scrutinized to find out the total number of Y, which is expressed as YMIN (s204). If the actual length of one division in the X direction is 1 mm, the shortest seal length LMIN is obtained by YMIN×1 mm (s205).

Figure 13:
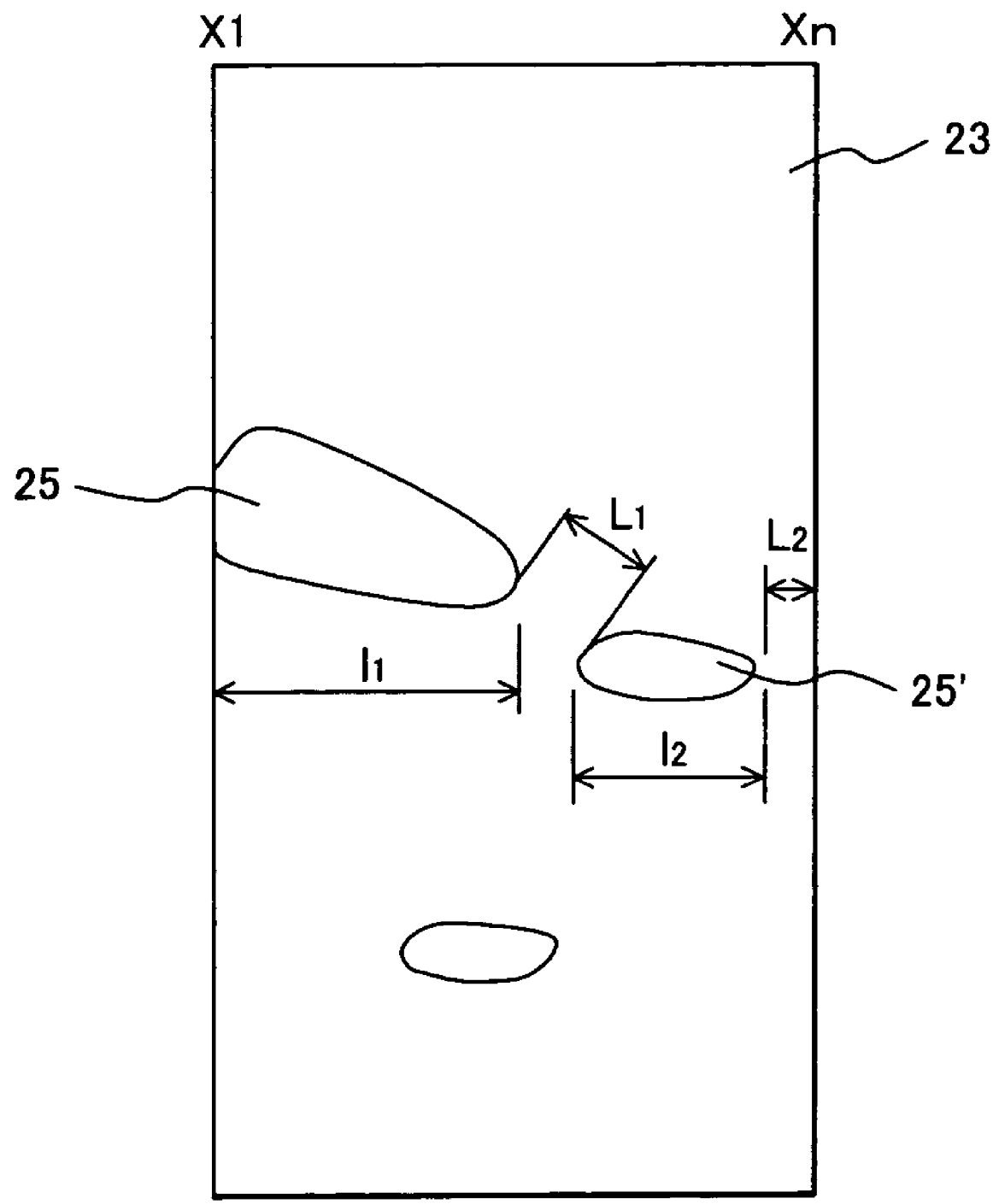
FIG. 13 is a diagram showing an evaluation of the connecting portion of the electrical winding in Example 1.

FIG. 13 shows a method of calculation of LMIN. If a brazing defect 25 having a length of $l_1$ adjoins a brazing defect 25' having a length $l_2$ in the plane screen having a width of X1 to Xn, a length L1 between the defects 25, 25' and the minimum length L2 between the defect 25' and Xn are calculated. The minimum sound portion length LMIN is obtained as a sum of L1 plus L2. The longer the sound portion length LMIN, the higher the mechanical strength of the connecting portion is obtained.

The defect portion is correctly displayed in the form of patterns. The connected rate CR and the minimum seal length LMIN are obtained from the measurement results; thus the processing of the evaluation mechanism 30 is finished.

Figure 14:
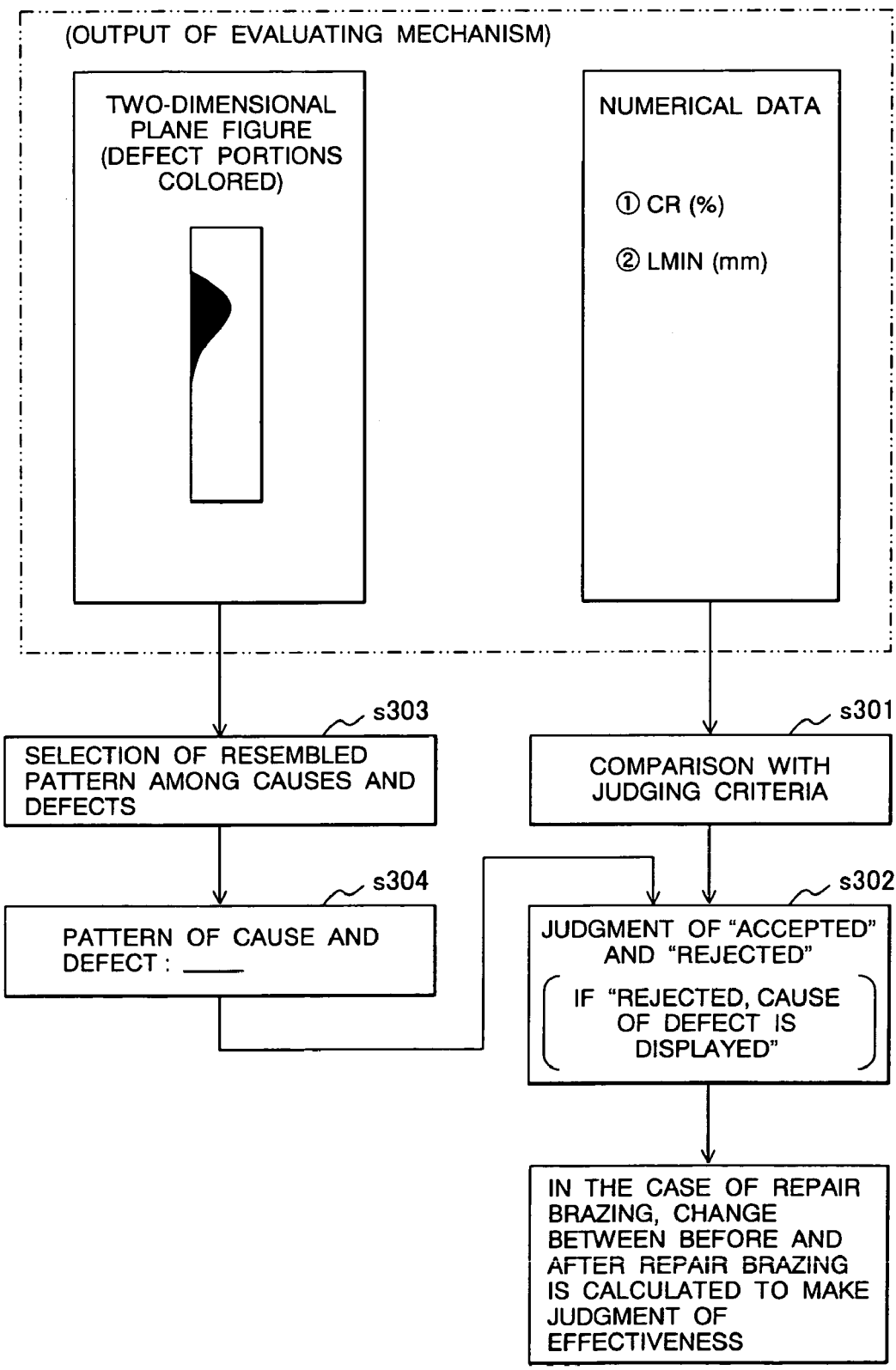
FIG. 14 is a flow chart showing the judging process of the connecting portion for the electrical winding in Example 1.

FIG. 14 shows a process of the judging mechanism. The data CR and LMIN obtained at the evaluation mechanism 30 are compared with previously designated judging criteria (s301), thereby to make a judgment of "accepted" or "not accepted" (s302).

According to the embodiment mentioned above, since the judgment of "accepted" or "not accepted" is made by reference to CR and LMIN, the connecting portions of the electrical windings are evaluated from the standpoints of electrical and mechanical points including leakage protection. Of course, the judgment can be made based on either CR or LMIN.

On the other hand, the defect occurring status of the brazing portions are displayed as patterns of causes of defects. The displayed patterns are compared with "typical patterns" to find similarity (s303) to select typical patterns with high similarity (s304). The selected patterns may be plural. The comparison of similarity between the displayed patterns and the typical patterns is made by extracting the relative relation of the two kinds of patterns. Of course, the comparison can be made by eye-observation.

FIG. 15 shows patterns based on cause-and-defect of the brazing portions, which are previously stored. FIG. 15 include names of patterns, typical patterns, status, causes, etc. For example, in the case of the stripe shape defect in pattern A, the end portion of the connecting sleeve 2 is generally sound, but there is a long, continuous defect in the central portion. This defect may possibly be caused by too much low temperature due to shortage of heating in the central portion. A large gap between the connecting sleeve 2 and the conductor 1 at the central portion may be another cause of the defect.

It is possible to choose a cause of the defect as a too much low temperature if the dimension records of the members are checked to find out whether the gap is proper or not. Further, a defect like a peninsula represents that a large defect is present at a particular position. This defect may possible be caused by an improper temperature distribution.

Basically, the guidelines or instruction for repair brazing may be acquired by try-and error methods. For example, if it is presumed that a defect is caused by brazing at a too much low temperature, a repair brazing is conducted at a relatively higher temperature. If a defect due to a too much high temperature, a second repair brazing at a relatively lower temperature is conducted thereby to achieve the targeted brazing connection. If the first repair brazing is not successive, the second repair brazing is conducted at a different condition such as a slightly lower temperature.

In addition to the try-and-error method, a repair brazing is conducted in accordance with guidelines previously stored in a memory device, an operator may select the most appropriate guideline. Of course, this method in accordance with the previously stored guidelines may be adopted besides the try-and-error method.

If the repair brazing needs a pretreatment such as degreasing or surface machining, the connected portion is disassembled so as to conduct the pretreatment.

As has been discussed, since causes are accumulated, based on the results of investigations, studies and arrangements of actual works, the causes of formation of brazing defects can easily be understood. If the actual works are compiled as data base, it is possible to obtain results with relatively stronger relative relation, and a higher probability of causes can be found out. Countermeasures to the causes are prepared, and they are displayed if necessary.

Since the judgment mechanism 40 judges the connecting result as "not accepted" and since the cause of the defect can be immediately found out, a policy of repair of the brazing is easily decided. If the repair of the brazing is done in accordance with the policy, measurement, evaluation and judgment are conducted again. The results are compared with the results previously obtained to calculate effects of the repair. Since the effects of the repair can be confirmed, it is possible to conduct improvement of the quality of the brazing.

In the case of the strip shape defect in No. A, for example, a repair brazing is conducted at a slightly lower set temperature. The results are measured and evaluated again. If the evaluation is "not accepted", changes of CR and LMIN are evaluated by the repaired article re-judgment mechanism. If the results are in the direction of improvement, the brazing temperature is further lowered to produce a brazing portion with a higher quality. By repetition of the loop shown in FIG. 1, it is possible to obtain desired quality of brazing.

On the other hand, brazing workers can concretely know where the causes of defects are, and know how the conditions are changed so as to alter the results. If the causes come from the brazing procedures, they can quickly know the results of the trial after the conditions are altered. At the same time, they can improve their ability or skill. As a result, it is possible to obtain a connecting method for electrical windings with improved, more proper quality.

According to the present invention, it is unnecessary, in general, to cut or break the product after manufacturing of the product so as to investigate the connected state; if the connected portion is judged as "not accepted", repair can be made to greatly reduce a cost of the product.

Next, the second example of the present invention (hereinafter referred to as Example 2) is explained. In a connecting conductor having a thickness of 1-10 mm, defects in the brazing portions occur in narrow gaps of 0.05 to 0.25 mm. Accordingly, by knowing the position of the defects and forming a narrow gate to the position, it is possible to precisely detect the defects.

In general, a surface echo in the detected portion is detected and the gate is disposed based on the surface echo; it is necessary to make the range of the gate wider if the distance between the surface and the defects changes. If not, a reflection echo from the object other than the defects may be detected.

Figure 16A:
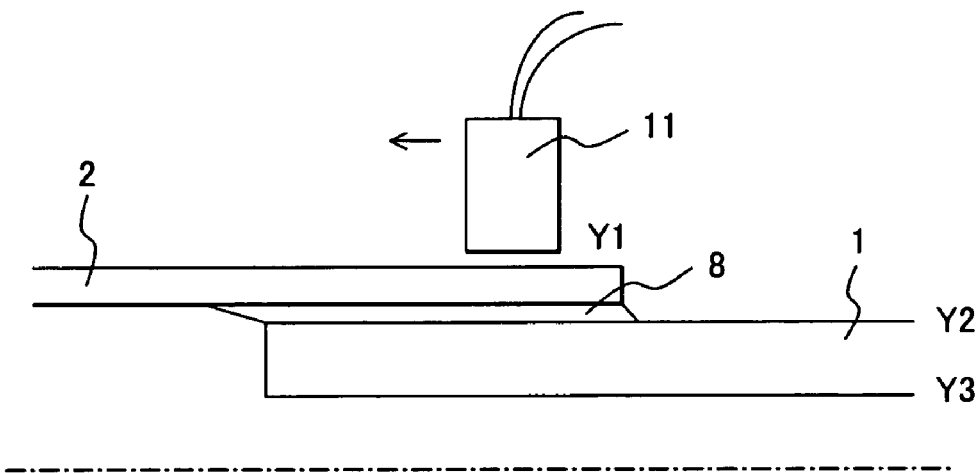
FIG. 16 is an explanatory drawing showing a cross sectional view of a method of measuring the connecting portion and reflection wave signal.

In Example 2, there is shown a disposition of the gate based on the bottom echo. FIG. 16 is an explanation figure for the bottom echo based gate. In FIG. 16(a), measurement of brazing portion wherein copper connecting sleeve 2 and a hollow conductor 1 are brazed by a brazing alloy 8 is conducted.

An ultrasonic wave beam impinged from the probe 11 to the connecting portion partly reflects at the outer surface Y2 of the sleeve 2 at first, and received by the probe 11. The remaining ultrasonic wave propagates in the sleeve 2 to arrive at the brazing portion; if there are brazing defects, the ultrasonic wave beam reflects at the interface Y2 (surface of the defects) and returns the probe 11 and is received. If there is not a brazing defect, the ultrasonic beam propagates into the interior of the hollow conductor 1 to arrive at the inner surface Y3 of the continuous hollow where the beam reflects and returns to the probe 11.

Figure 16B:
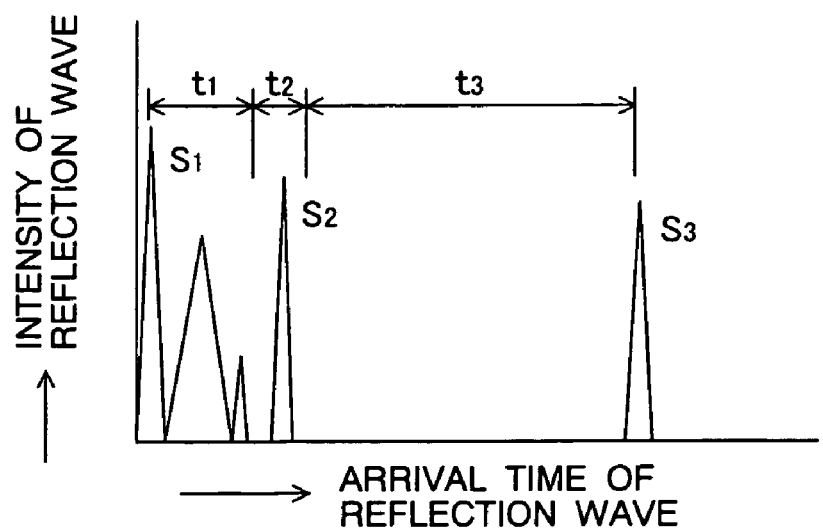

FIG. 16(b) shows a relationship between an intensity of reflection wave signals received by the probe 11 and time. The wider the area of the reflection wave signal of the ultrasonic wave beam, the stronger the intensity becomes. The longer the propagation, the longer the time to receive becomes longer. There is a relation between intensity and time, shown in FIG. 16(b), among the reflection wave signals S1, S2, S3 from the interfaces Y1, Y2, Y3.

In order to accurately measure the defects at the brazing portions, the probe 11 should have a function for focusing the ultrasonic wave beam as a spot in the vicinity of the brazing portion. A spread of the ultrasonic wave is suppressed; a range of depth at which the reflection wave arrives is set as a gate in advance; the reflection wave signal detected in the gate is utilized as data for evaluation of the brazing portion.

In Example 2, the standard position for setting the gate is positioned at the surface (Y3) of the continuous hollow of the hollow conductor.

Figure 17A:
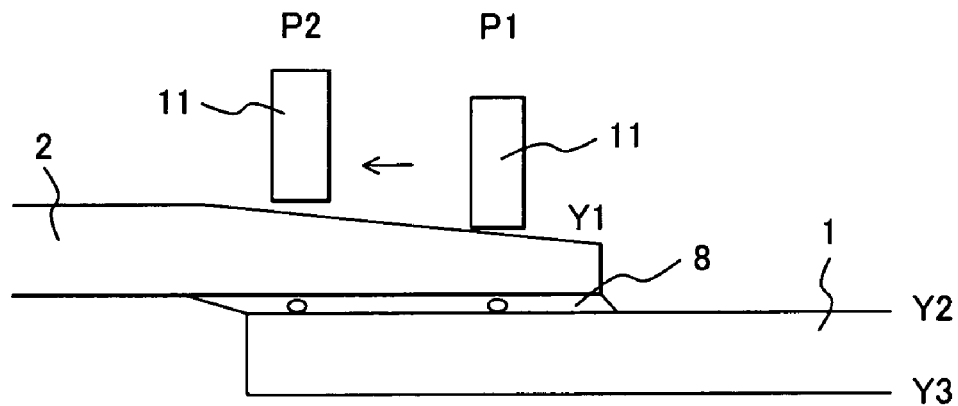
FIG. 17 is an explanatory drawing showing a cross sectional view of another example in Example 2.
Figure 17B:
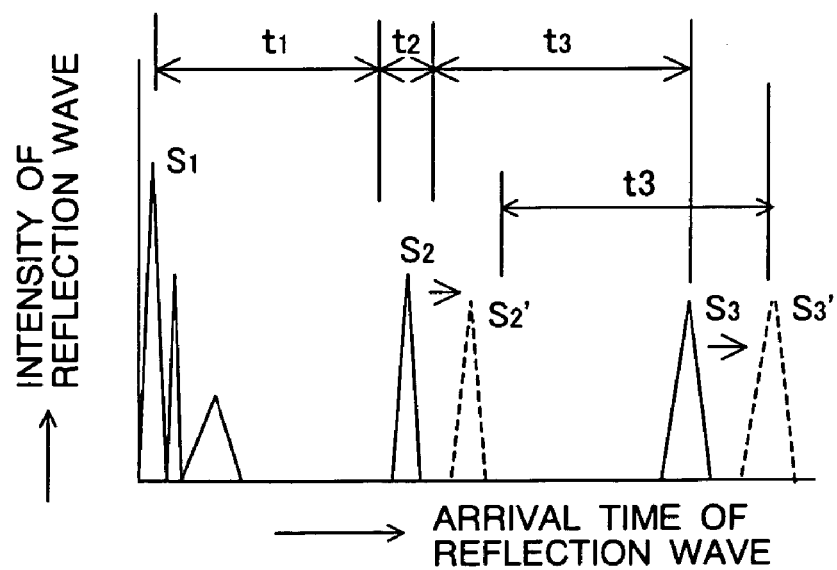

FIG. 17 is an explanation of forming the bottom echo standard gate. As shown in FIG. 17(a), the thickness of the connecting sleeve 2 changes at the positions of P1 and P2. In this case, as shown in FIG. 17(b), the propagation time difference i.e. t1: (time difference between S1-S2) between the reflection wave signal S1 from the surface (Y1) and the reflection wave signal S2 from the brazing portion (Y2) changes since S2 shifts to S2'. Accordingly, setting positions of the surface standard echo gate are changed by chance or the gate is set wider.

In Example 2, the gate time width t2 is fixedly set based on the time difference t3 between the reflection wave signal S3 from the hollow surface (Y3) as the standard and the reflection wave signal S2 from the brazing defect. According to this method, it is not necessary to change or widen the gate time width t2, even if the thickness of the sleeve 2 changes. Thus, it is possible to detect and measure the defects precisely. If a large defect is present whereby the reflection wave signal S3 is not detected effectively, the surface echo standard gate can be employed.

Figure 18:
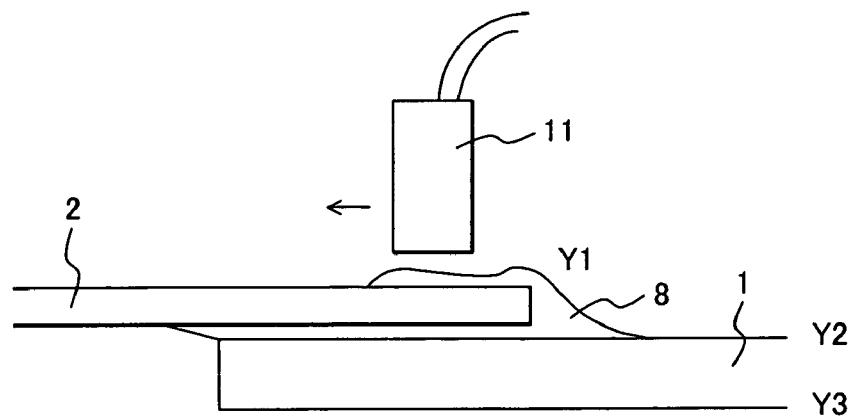
FIG. 18 is an explanatory drawing showing a cross sectional view of still another example of application in Example 2.

As shown in FIG. 18, where an excess brazing material 8 adheres to the surface outside of the connecting sleeve 2, it is considered as equivalent to the change of thickness of the sleeve; thus it is possible to measure, according to Example 2.

Figure 19:
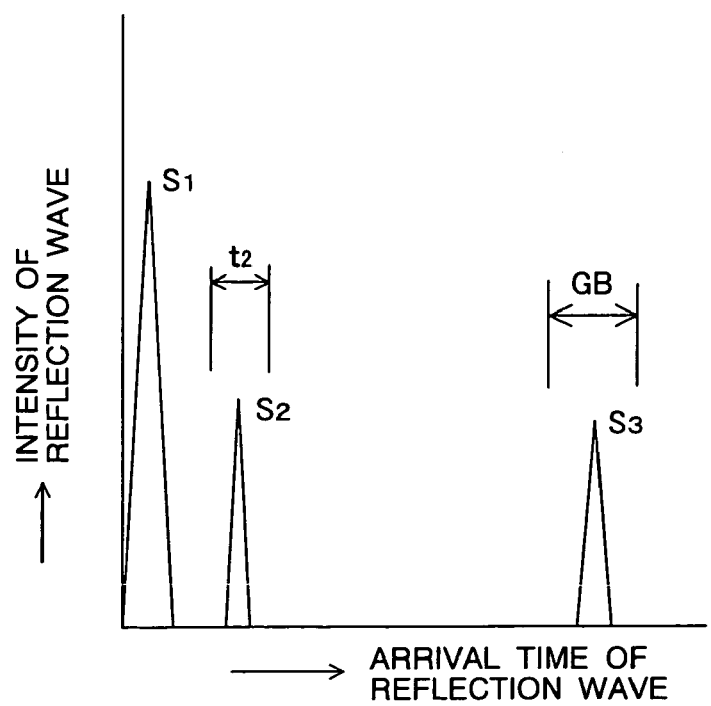
FIG. 19 is an explanation of an evaluation method of a connecting portion in Example 3.

The third example (hereinafter referred to as Example 3) will be explained. FIG. 19 shows a gate time according to Example 3. In this Example, gate: GB for reflection wave signal S3 from the hollow surface is set, and the reflection wave signal S2 from the brazing portion and the reflection wave signal S3 (bottom echo) are always measured.

When the defect area of the brazing portion is wide, S2 becomes large and, on the other hand, the bottom echo S3 becomes small since part of the ultrasonic wave that propagates in the hollow conductor 1 reduces. When the brazing defect is small, there may be a case where the reflection wave signal S2 is small or S3 is not detected because S2 is smaller than the detection limit; in the above case, the reflection wave signal S3 is large and detected. These examples are all normal.

However, in case where the reflection wave signal S2 is not detected, this is not always meant that there are no defects. For example, there may be a possibility that the probe 11 separates from the sleeve 2 so that the ultrasonic wave does not propagate. Accordingly, if the reflection wave signal is not detected, it is necessary to confirm whether the ultrasonic wave has surely propagated by confirming the existence and measurement of the reflection wave signal S3.

In Example 3, it is proved that the measurement results are judged as being correct when the reflection wave signal S3 is measured, but the reflection wave signal S2 is not measured at the position where S3 exists.

Figure 20:
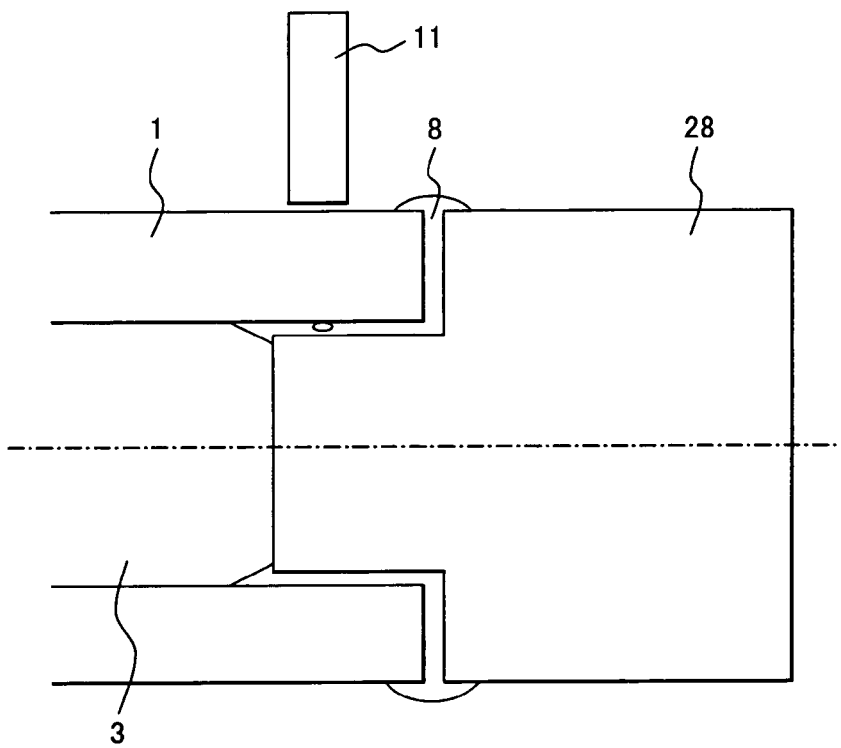
FIG. 20 is an explanation of a measuring method of connecting portion in Example 4.

The fourth example (hereinafter referred to as Example 4) in which the hollow conductor and the solid conductor are brazing-connected will be explained. FIG. 20 shows a structure to which Example 4 of the present invention is applied. Compared with Example 1, the conductor 28 (right hand) is a solid conductor and the conductor 1 (right hand) is the hollow conductor.

Figure 21:
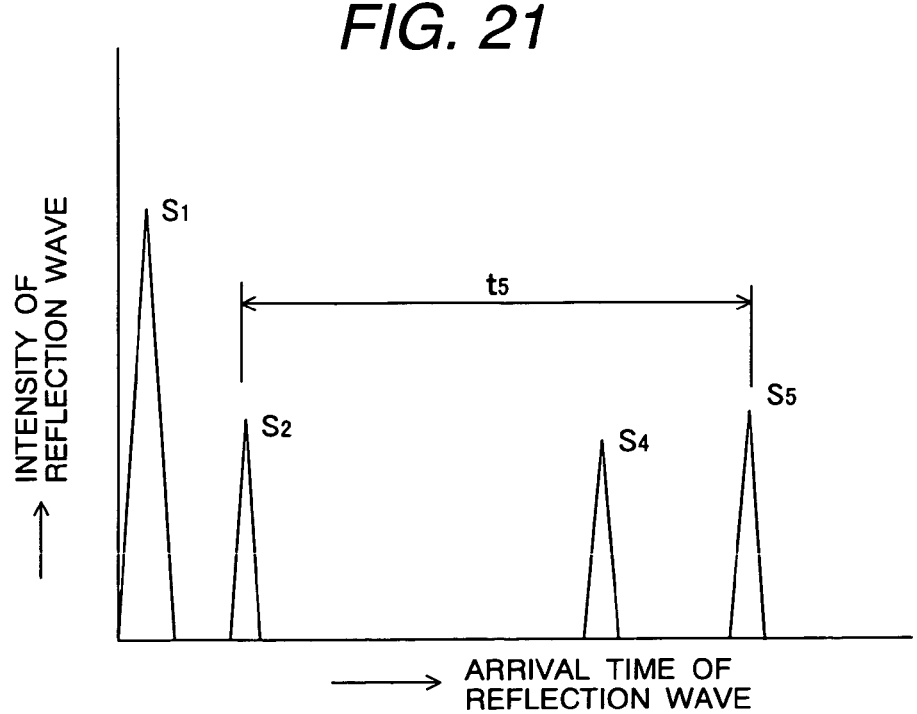
FIG. 21 is an explanation of an evaluation method of a connecting portion in Example 4.

FIG. 21 shows a mechanism of reflecting wave in Example 4. The bottom echo generates from the outer surface of the opposite side of the conductor 28 and becomes reflection wave signal S5. There are two brazing faces between the surface echo S1 and the bottom echo S5. If there are defects, reflection wave signals S2, S4 from the defects are observed.

In Example 4, if the reflection wave signal S2 is selected as the measurement object, and if the gate is set to that position, it is possible to measure and evaluate, the same as in Example 2. If the reflection wave signal S5 is selected as the bottom echo, and if the propagation of the ultrasonic wave is confirmed, it is possible to obtain the same effect as in Example 3.

As having been explained, according to Examples 1 to 4, since bonding portions of electrical windings with high reliability are produced, the life of the windings is extended and the long term operation of electric machines is expected, and a cost of operation will be reduced.

What is claimed is:

1. A method of evaluating a connected portion of electrical winding conductors of an electric machine, comprising:
    probing a brazed state of the connected portion with an ultrasonic wave,
    detecting reflection wave signals reflected from the connected portion by the probing step,
    judging sound portions and defect portions of the connected portion in the results of the detecting step,
    displaying results of the judging step so as to indicate the sound portions and defect portions of the connected portion,
    discriminating the sound portions and defect portions of the connected portion in the results of the judging step, and
    evaluating the connected portion by comparing the discriminated results with patterns previously stored in a memory device, based on predetermined criteria.

2. The method of evaluating a connected portion of electrical winding according to claim 1, wherein the conductors are aligned in a longitudinal direction.

3. The method of evaluating a connected portion of electrical winding conductors according to claim 1, wherein the evaluating step is conducted based on an area of the defect portions and a length of the sound portions.

4. The method of evaluating a connected portion of electrical winding conductors according to claim 1, wherein the defect portions are compared with the stored patterns to determine a cause of the related defects, and the cause is output when the connected portion is evaluated as being not accepted.

5. The method of evaluating a connected portion of electrical winding conductors according to claim 1, wherein the detected reflection wave signals are restricted within a range of a gate time.

6. The method of evaluating a connected portion of electrical winding conductors according to claim 1, wherein the reflection wave signals that come from the brazing portion of an inner object are evaluated.

7. A method of connecting electrical winding conductors of an electric machine, comprising:
    connecting a pair of electrical winding conductors of the electrical machine with a brazing alloy, at least one of the conductors having a continuous hollow in a longitudinal direction,
    probing a brazed state of the connected portion with an ultrasonic wave signal,
    discriminating sound portions and defect portions of the connected portion,
    displaying results of the discriminating step, and
    evaluating the connected portion by comparing the discriminated results with patterns previously stored in a memory device, based on predetermined criteria.

8. The method of evaluating a connected portion of electrical winding according to claim 7, wherein the conductors are aligned in a longitudinal direction.

9. The method of connecting electrical winding conductors according to claim 7, wherein the evaluating step is conducted based on an area of the defect portions and a length of the sound portions.

10. The method of connecting electrical winding conductors according to claim 7, wherein the connected portion is brazed again in accordance with a method for improving quality of the connected portion, a newly connected state of the brazed portion is probed again with the ultrasonic wave, and the difference between the previous brazing and the new brazing is displayed.

11. The method of connecting electrical winding conductors according to claim 7, wherein when a defect portion is not detected, the soundness/defectiveness of the connected portion is judged by evaluation of the reflected wave signals coming from the inner surface of the winding conductor located inside among the winding conductors to be connected.

12. A connecting apparatus for connecting a pair of electrical winding conductors with a brazing alloy, at least one of the conductors having a continuous hollow in a longitudinal direction, which comprises:
    a connecting mechanism including a holding mechanism for holding the conductors, a heating source for heating a connecting portion, and a brazing alloy supply mechanism for supplying a brazing alloy to the connecting portion,
    a measuring mechanism for probing a connected portion with an ultrasonic wave,
    a means for discriminating sound portions and defect portions of the connected portion,
    a display device for displaying patterns of the sound portions and defect portions, and
    an evaluation device for evaluating the connected portion based on an area of the defect portions and a length of the sound portions.

13. The method of evaluating a connected portion of electrical winding according to claim 12, wherein the conductors are aligned in a longitudinal direction.

14. The connecting apparatus for connecting electrical winding conductors according to claim 12, which further comprises a judging device, which has stored patterns of cause-and-defect, for comparing the defect portions with the cause-and-defect patterns and displaying the related cause of the defects.

15. The connecting apparatus for connecting electrical winding conductors according to claim 12, further comprising a re-judging device for judging, when the connected portion is evaluated as being not-sound, a difference between the previous connecting and a new connecting and displaying the difference, after re-connecting the connected portion using the connecting mechanism.

16. A connecting apparatus for connecting a pair of electrical winding conductors with a brazing alloy, at least one of the conductors having a continuous hollow in the longitudinal direction, which comprises: a connecting mechanism including a holding mechanism for holding the conductors, a heating source for heating a connecting portion, and a brazing alloy supply mechanism for supplying a brazing alloy to the connecting portion; a measuring mechanism for probing a connected portion with an ultrasonic wave; a means for discriminating sound portions and defect portions of the connected portion; a display device for displaying patterns of the sound portions and defect portions; and an evaluation device for evaluating the connected portion based on an area of the defect portions and a length of the sound portions, wherein the measuring mechanism comprises a scanner having an ultrasonic probe for moving the probe in at least two dimensional directions, and a holder, which supports the scanner and carries the ultrasonic probe to the connected portion, and wherein the scanner and the holder are previously separated, whereby the scanner and the holder are assembled after the holder is disposed to the electrical winding conductors close to the connected portion to be measured.

17. A connecting apparatus for connecting a pair of electrical winding conductors with a brazing alloy, at least one of the conductors having a continuous hollow in the longitudinal direction, which comprises: a connecting mechanism including a holding mechanism for holding the conductors, a heating source for heating a connecting portion, and a brazing alloy supply mechanism for supplying a brazing alloy to the connecting portion; a measuring mechanism for probing a connected portion with an ultrasonic wave; a means for discriminating sound portions and defect portions of the connected portion; a display device for displaying patterns of the sound portions and defect portions; and an evaluation device for evaluating the connected portion based on an area of the defect portions and a length of the sound portions, wherein the measuring device further comprises a bottom echo standard gate for detecting a defect portion as a criterion based on reflection wave signals coming from the inner conductor among the electrical winding conductors to be connected.

18. An ultrasonic wave testing method for probing a brazed connected portion of objects with an ultrasonic wave, which comprises setting a gate time for restricting a width of a detecting reflecting wave signal coming from the connected portion and a signal coming from an inner object as a criterion based on the reflection wave, probing a brazed state of the connected portion with an ultrasonic wave, detecting reflection wave signals reflected from the connected portion by the probing step, judging sound portions and defect portions of the connected portion in the results of the judging step, displaying results of the judging step so as to indicate the sound portions and defect portions of the connected portion, discriminating the sound portions and defect portions of the connected portion in the results of the judging step, and evaluating the connected portion by comparing the discriminated results with patterns previously stored in a memory device, based on predetermined criteria, wherein the patterns are cause-and-defect patterns thereby to determine a cause of the defects, and the cause is output when the connected portion is evaluated as being not accepted.

19. An evaluation apparatus for evaluating a connected portion of electrical winding conductors, at least one of the conductors having a continuous hollow extending in a longitudinal direction, which comprises:
a measuring mechanism for probing a connected portion with an ultrasonic wave,
a means for discriminating sound portions and defect portions of the connected portion,
a display device for displaying patterns of the sound portions and defect portions, and
an evaluation device for evaluating the connected portion based on an area of the defect portions and a length of the sound portions by means of cause-and-defect patterns stored in a memory.

20. The evaluating apparatus according to claim 19, wherein the conductors are aligned in a longitudinal direction.

21. A method of evaluating a connected portion of electrical wiring conductors of an electric machine, comprising the steps of:
probing a brazed stated of the connected portion with an ultrasonic wave,
detecting reflection wave signals reflected from the connected portion by the probing step,
judging sound portions and defect portions of the connected portion in the results of the detecting step,
displaying results of the judging step so as to indicate the sound portions and defect portions of the connected portion,
discriminating the sound portions and defect portions of the connected portion in the results of the judging step, and
evaluating the connected portion by comparing the discriminated results with patterns previously stored in a memory device, based on predetermined criteria,
wherein the patterns are cause-and-defect patterns thereby to determine a cause of the related defects, and the cause is output when the connected portion is evaluated as being not accepted.

22. A method of connecting electrical winding conductors of an electric machine comprising:
connecting at least a pair of electrical conductors of the electrical machine with a brazing alloy, at least one of the conductors having a continuous hollow in a longitudinal direction thereof,
probing a brazed state of the connected portion with an ultrasonic wave,
detecting reflection wave signals reflected from the connected portion by the probing step,
displaying results of the detecting step so as to indicate sound portions and defect portions of the connected portion,
discriminating sound portions and defect portions of the connected portion in the results of the detecting step, and
evaluating the connected portion by comparing the discriminated results with cause-and-defect patterns previously stored in a memory device, based on predetermined criteria, wherein the connected portion is brazed again in accordance with a method for improving quality of the connected portion, a newly connected state of the brazed portion is probed again with the ultrasonic wave, and the difference between the brazing and the new brazing is displayed.

23. A method of connecting electrical winding conductors, comprising the steps of:
connecting electrical winding conductors with a brazing material to create a connected portion;
conducting an ultrasonic wave inspection over the connected portion;
displaying a sound portion and a defect portion of the portion inspected by the conducting step, by discriminating results of the inspection; and
evaluating a brazing state of defect portions discriminated as a result of the inspection, based upon predetermined criteria, by comparing the brazing state with cause-and-defect patterns previously stored in a memory.

24. The method of connecting electrical winding conductors according to claim 23, wherein the evaluation is conducted based on an area of the defect portion and a length of the sound portion.

25. The method of connecting electrical winding conductors according to claim 23, wherein the defect portion is compared with patterns of causes of the defect that have been stored previously in the memory, and related causes of the defect and countermeasures for improving the brazing quality are displayed.

26. The method of connecting electrical winding conductors according to claim 25, wherein the connecting of the winding conductors at the defect portion is conducted again in accordance with the displayed countermeasures for improving the brazing quality after ultrasonic inspection of the connected defect portion, and the difference between the first brazing and the second brazing is displayed.

27. The method of connecting electrical winding conductors according to claim 23, wherein when no defect portion is detected, a reflection wave of the ultrasonic wave inspection reflected from the winding conductor in the inner side of the winding conductors is detected to evaluate the ultrasonic inspection.

* * * * *